United States Patent
Lin et al.

(10) Patent No.: US 8,729,055 B2
(45) Date of Patent: May 20, 2014

(54) URSOLIC ACID DERIVATIVE AND PHARMACEUTICAL COMPOSITION THEREOF

(75) Inventors: Chun-Nan Lin, Kaohsiung (TW);
Huang-Yao Tu, Kaohsiung (TW);
A-Mei Huang, Kaohsiung (TW);
Bai-Luh Wei, Kaohsiung (TW);
Kim-Hong Gan, Kaohsiung (TW);
Tzyh-Chyuan Hour, Kaohsiung (TW);
Shyh-Chyun Yang, Kaohsiung (TW);
Yeong-Shiau Pu, Kaohsiung (TW);
Shen-Jeu Won, Kaohsiung (TW)

(73) Assignee: Kaohsiung Medical University, Kaohsiung City (TW)

( * ) Notice: Subject to any disclaimer, the term of this patent is extended or adjusted under 35 U.S.C. 154(b) by 746 days.

(21) Appl. No.: 12/782,395

(22) Filed: May 18, 2010

(65) Prior Publication Data

US 2011/0190388 A1    Aug. 4, 2011

(30) Foreign Application Priority Data

Feb. 2, 2010 (TW) ............................. 099103086 A

(51) Int. Cl.
*A61K 31/56* (2006.01)
*A61K 31/58* (2006.01)
*A61K 31/585* (2006.01)

(52) U.S. Cl.
CPC ................. *A61K 31/56* (2013.01); *A61K 31/58* (2013.01); *A61K 31/585* (2013.01)
USPC ........................................... 514/169; 514/175

(58) Field of Classification Search
CPC ...... A61K 31/585; A61K 31/56; A61K 31/58
USPC .................................................. 514/169, 175
See application file for complete search history.

(56) References Cited

U.S. PATENT DOCUMENTS 3,903,089 A * 9/1975 Vanstone ...................... 544/380

OTHER PUBLICATIONS

Finlay et al., Bioorganic & Medicinal Chemistry Letters, 1997;7(13):1769-1772.*
Stella et al., Drugs, 1985;29:455-473.*
Rautio et al., Nature, 2008;7:255-270.*

* cited by examiner

*Primary Examiner* — San-Ming Hui
(74) *Attorney, Agent, or Firm* — Volpe and Koenig, P.C.

(57) ABSTRACT

Several ursolic acid derivatives and pharmaceutical compositions thereof are provided. The ursolic acid derivatives and the pharmaceutical compositions thereof have at least one of an anticancer and an anti-inflammatory effects. A method for increasing a reactive oxygen species in a cell is also provided. The method comprises a step of providing the cell with a pharmaceutical composition including an ursolic acid derivative.

7 Claims, 5 Drawing Sheets

URSOLIC ACID DERIVATIVE AND PHARMACEUTICAL COMPOSITION THEREOF

FIELD OF THE INVENTION

The present invention relates to a compound and a pharmaceutical composition thereof, and more particularly to ursolic acid derivatives and pharmaceutical compositions thereof.

BACKGROUND OF THE INVENTION

Triterpenoids abundantly exist in plant kingdom, wherein the ursolic acid and the derivatives thereof have been reported to have antitumor, anti-inflammatory, antiviral and antioxidant activities.

Reactive oxygen species (ROS) are resulting in oxidation of various cell constituents as DNA, lipid and proteins, and consequently these oxidations may cause damage to the cellular substance leading to cell death as the ultimate consequence. ROS have been implicated in a number of disease including various forms of non-hormone dependent cancers, atherosclerosis, ischemic reperfusion injury, neurodegenerative diseases, chronic inflammatory disease, such as rheumatoid and psoriatic arthritis, and some factors underlying the aging process itself. ROS might also play a role as signaling molecules and as such they may have a role in cell cycle progression.

Several anticancer agents, such as arsenic trioxide, doxorubicin, bleomycin, cisplatin, 5-Fu, and paclitaxel have been shown to induce ROS generation in cancer cells. Various mechanisms have been described, including respiratory chain disruption, redox cycling, or p53-mediated mitochondrial oxidase activation.

Recently, several compound structures and cytotoxic relationships have been reported. However, a series of structures and cytotoxic relationships of ursolic acid derivatives did not appear in literature. Accordingly, there is a need to evaluate the cytotoxicities against tumor cells, the structures and cytotoxic relationships and mechanisms of action of ursolic acid derivatives.

SUMMARY OF THE INVENTION

In accordance with one aspect of the present invention, an ursolic acid derivative is provided, which has a structure being one selected from a group consisting of

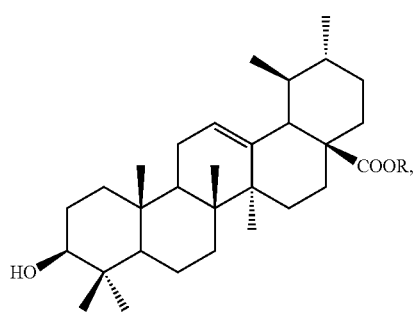

I

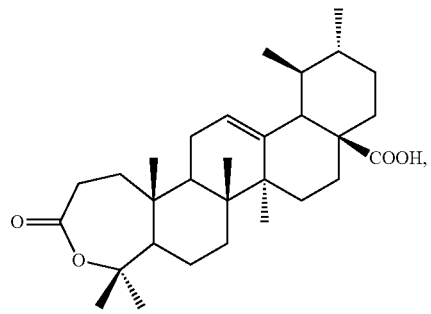

II

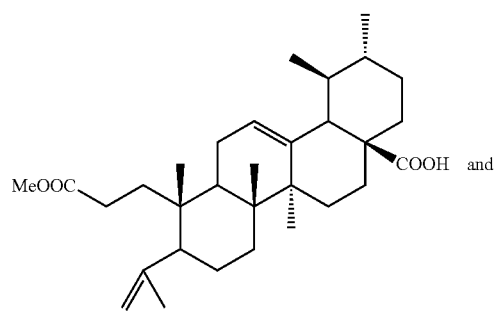

III

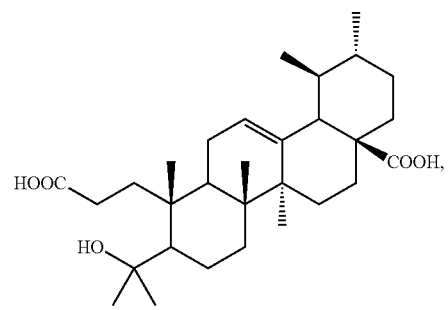

IV wherein R is one selected from a group consisting of a $C_5$-$C_{12}$ alkyl group, $CH(CH_3)_2$,

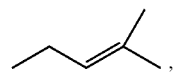

an alcohol group and $CH_2COOC(CH_3)_3$.

Preferably, the $C_5$-$C_{12}$ alkyl group is one of $CH_2CH_2CH_2CH_2CH_3$ and $CH_2CH_2CH_2CH_2CH_2CH_3$.

Preferably, the alcohol group is $CH_2CH_2OH$.

Preferably, the ursolic acid derivative has at least one of an anticancer and an anti-inflammatory activities.

In accordance with another aspect of the present invention, a pharmaceutical composition comprising the mentioned ursolic acid derivative is provided.

Preferably, the pharmaceutical composition further comprises a pharmaceutically acceptable carrier.

Preferably, the pharmaceutical composition has at least one of an anticancer and an anti-inflammatory effects.

Preferably, the pharmaceutical composition further comprises a drug having an anticancer activity, and the ursolic acid derivative enhances the anticancer activity of the drug.

In accordance with a further aspect of the present invention, a method for inducing at least one of an anticancer and an anti-inflammatory effects is provided. The method comprises a step of administering to a subject in need thereof an effective amount of the mentioned pharmaceutical composition.

Preferably, the method further comprises a step of administering to the subject an effective amount of a drug having an anticancer activity, wherein the pharmaceutical composition enhances the anticancer activity of the drug.

Preferably, the pharmaceutical composition further includes a pharmaceutically acceptable carrier.

In accordance with a further aspect of the present invention, a method for increasing a reactive oxygen species (ROS) in a cell is provided. The method comprises a step of providing the cell with a pharmaceutical composition including an ursolic acid derivative.

Preferably, the pharmaceutical composition further includes a pharmaceutically acceptable carrier.

Preferably, the ursolic acid derivative has a structure being one selected from a group consisting of formulas I, II, III and IV.

Preferably, the cell is a tumor cell.

Twenty-three ursolic acid derivatives are synthesized in the present invention, and several synthetic compounds indicate significant cytotoxic effects against NTUB1 cells. Compounds 5 and 23 reveal a partial mechanism by which 5 and 23 mediated through generation of ROS in NTUB1 cells induce inhibition of tubulin polymerization, G2/M and G1 cell cycle arrest, and apoptosis. The present invention facilitates the development of novel, efficient, and less toxic anticancer agents targeting microtubules.

The above objects and advantages of the present invention will become more readily apparent to those ordinarily skilled in the art after reviewing the following detailed descriptions and accompanying drawings, in which:

DETAILED DESCRIPTION OF THE PREFERRED EMBODIMENT

The present invention will now be described more specifically with reference to the following embodiments. It is to be noted that the following descriptions of embodiments of this invention are presented herein for the purposes of illustration and description only; it is not intended to be exhaustive or to be limited to the precise form disclosed.

Compounds having at least one of an anticancer and an anti-inflammatory effects are provided. The compounds are ursolic acid derivatives, and the synthetic processes thereof are described as follows.

EXAMPLE 1

This example illustrates the preparation of compounds 1-11.

Figure 1:
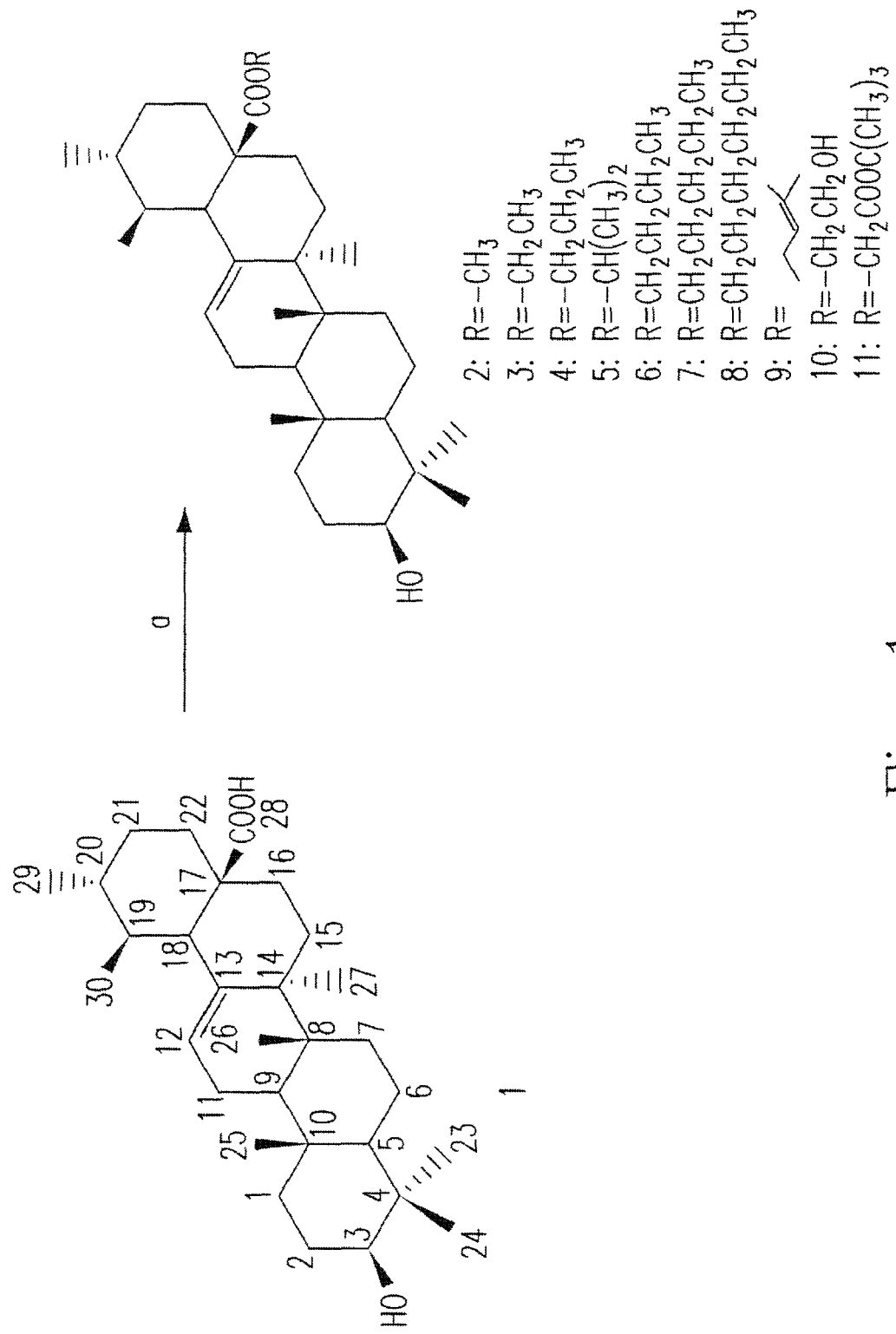
FIG. 1 is a flow chart illustrating the processes in the present invention for synthesizing the compounds 2-11, wherein each number represents a different compound.

Please refer to FIG. 1, which is a flow chart illustrating the processes in the present invention for synthesizing the compounds 2-11, wherein each number represents a different compound.

The material of compound 1 is obtained from leaves of loquat (*Eriobotrya japonica*). A modified method for extracting ursolic acid from leaves of loquat to isolate large amount of ursolic acid is provided in the present invention. Leaves of loquat (10 kg) are extracted by methanol. The MeOH extract is shaken under ultrasonic wave for 90 min at 50° C. The extract is added 1% NaOH solution to form salt and filtered. The solution is neutralized with c-HCl to afford light yellow solid. The solid is purified by silica gel chromatography and recrystallized for several times to give compound 1 (21.9 g).

Compound 1 is used as the starting material for synthesizing the compounds 2-11. To a solution of compound 1 (30 mg, 0.07 mmol) in acetone is added $K_2CO_3$ (20 mg, 0.14 mmol) and different alkyl halide (0.14 mmol). The reaction mixture is stirred at the room temperature overnight. The mixture is concentrated to dryness under reduced pressure, diluted with water (30 mL), and extracted with DCM (30 mL×3). The organic phase is dried over $Na_2SO_4$, filtered, and concentrated in vacuo to give the crude product. The crude product is purified by chromatography using EtOAc/n-hexane to afford purified compounds 2-11.

The detailed embodiments for the preparation of the compounds 5 and 7-11 are described as follows.

Isopropyl 3β-hydroxyurs-12-en-28-oate (compound 5): Compound 5 is prepared from compound 1 (50 mg, 0.11 mmol) following the general procedure described for esterification at C-17 carboxylic acid using isopropyl iodide as alkyl halide moiety. Compound 5 was obtained as a white solid (49.2 mg, 0.10 mmol, 90%), $[\alpha]_D^{25}$=+50. IR (KBr): 3447, 1715 cm$^{-1}$. $^1$H NMR (CDCl$_3$): δ 0.77 (3H, m, H-24), 0.82 (3H, s, H-25), 0.85 (3H, d, J=6.4 Hz, H-30), 0.91 (3H, s, H-26), 0.93 (3H, d, J=6.4 Hz, H-29), 0.98 (3H, s, H-27), 1.07 (3H, s, H-23), 1.16 (3H, d, J=6.0 Hz, —CH(CH$_3$)$_2$), 1.19 (3H, d, J=6.0 Hz, —CH(CH$_3$)$_2$), 2.21 (1H, d, J=11.2 Hz, H-18), 3.21 (1H dd, J=10.8, 5.2 Hz, H-3α), 4.91 (1H, m, —CH(CH$_3$)$_2$), 5.24 (1H, t, J=4.0 Hz, H-12). $^{13}$C NMR (CDCl$_3$): δ 15.5 (C-24), 15.6 (C-25), 17.0 (C-11), 17.3 (C-26), 18.3 (C-6), 21.2 (C-29), 21.7 (—CH(CH$_3$)$_2$), 21.8 (—CH(CH$_3$)$_2$), 23.3 (C-27), 23.4 (C-30), 24.1 (C-16), 27.2 (C-2), 28.0 (C-15), 28.1 (C-23), 30.7 (C-21), 33.2 (C-7), 36.6 (C-22), 36.9 (C-10), 38.6 (C-4), 38.7 (C-1), 38.9 (C-20), 39.1 (C-19), 39.6 (C-8), 42.1 (C-14), 47.6 (C-9), 47.7 (C-17), 52.8 (C-18), 55.2 (C-5), 66.9 (—COOCH(CH$_3$)$_2$), 79.0 (C-3), 125.5 (C-12), 138.1 (C-13), 176.9 (C-28). EIMS (70 eV) m/z (% rel. int.): 498 [M]$^+$ (3). HREIMS: calcd for C$_{33}$H$_{54}$O$_3$: 498.4073. found: 498.4071.

Pentyl 3β-hydroxyurs-12-en-28-oate (compound 7): Compound 7 is prepared from compound 1 (50 mg, 0.11 mmol) following the general procedure described for esterification at C-17 carboxylic acid using pentyl iodide as alkyl halide moiety. Compound 7 is obtained as a white solid (48.5 mg, 0.09 mmol, 84%), $[\alpha]_D^{25}$=+38. IR (KBr): 3447, 1718 cm$^{-1}$. $^1$H NMR (CDCl$_3$): δ 0.75 (3H, s, H-25), 0.77 (3H, s, H-24), 0.85 (3H, d, J=6.4 Hz, H-30), 0.91 (3H, s, H-26), 0.91 (3H, t, J=7.2 Hz, —CH$_2$CH$_3$), 0.93 (3H, d, J=6.4 Hz, H-29), 0.98 (3H, s, H-27), 1.07 (3H, s, H-23), 2.22 (1H, d, J=10.8 Hz, H-18), 3.21 (1H, dd, J=10.8, 4.8 Hz, H-3α), 3.97 (2H, m, —COOCH$_2$—), 5.23 (1H, t, J=3.6 Hz, H-12). $^{13}$C NMR (CDCl$_3$): δ 14.0 (—CH$_2$CH$_3$), 15.4 (C-24), 15.6 (C-25), 17.0 (C-11), 17.1 (C-26), 18.3 (C-6), 21.2 (C-29), 22.3 (—CH$_2$CH$_3$), 23.3 (C-27), 23.5 (C-30), 24.2 (C-16), 27.2 (C-2), 28.0 (C-15), 28.1 (—CH$_2$CH$_2$CH$_3$), 28.2 (C-23), 28.3 (—OCH$_2$CH$_2$—), 30.7 (C-21), 33.0 (C-7), 36.7 (C-22), 36.9 (C-10), 38.6 (C-1), 38.7 (C-4), 38.9 (C-20), 39.1 (C-19), 39.5 (C-8), 42.0 (C-14), 47.5 (C-9), 48.0 (C-17), 52.8 (C-18), 55.2 (C-5), 64.3 (—COOCH$_2$—), 79.0 (C-3), 125.5 (C-12), 138.2 (C-13), 177.6 (C-28). EIMS (70 eV) m/z (% rel. int.): 526 [M]$^+$ (3). HREIMS: calcd for C$_{35}$H$_{58}$O$_3$: 526.4385. found: 526.3910.

Hexyl 3β-hydroxyurs-12-en-28-oate (compound 8): Compound 8 is prepared from compound 1 (50 mg, 0.11 mmol) following the general procedure described for esterification at C-17 carboxylic acid using hexyl iodide as alkyl halide moiety. Compound 8 is obtained as a white solid (26.5 mg, 0.05 mmol, 45%), $[\alpha]_D^{25}$=+34. IR (KBr): 3446, 1718 cm$^{-1}$. $^1$H NMR (CDCl$_3$): δ 0.75 (3H, s, H-25), 0.77 (3H, s, H-24), 0.86 (3H, t, J=7.6 Hz, —CH$_2$CH$_3$), 0.88 (3H, d, J=6.4 Hz, H-30), 0.91 (3H, s, H-26), 0.93 (3H, d, J=6.4 Hz, H-29), 0.98 (3H, s, H-27), 1.07 (3H, s, H-23), 2.22 (1H, d, J=11.2 Hz, H-18), 3.21 (1H, dd, J=9.6, 4.8 Hz, H-3α), 3.97 (2H, m, —COOCH$_2$—), 5.23 (1H, t, J=3.6 Hz, H-12). $^{13}$C NMR (CDCl$_3$): δ 14.0 (—CH$_2$CH$_3$), 15.4 (C-24), 15.6 (C-25), 17.0 (C-11), 17.1 (C-26), 18.3 (C-6), 21.2 (C-29), 22.6 (—CH$_2$CH$_3$), 23.3 (C-27), 23.5 (C-30), 24.2 (C-16), 25.7 (OCH$_2$CH$_2$CH$_2$—), 27.2 (C-2), 28.0 (C-15), 28.1 (C-23), 28.5 (—CH$_2$CH$_2$CH$_3$), 30.7 (C-21), 31.4 (—OCH$_2$CH$_2$—), 33.0 (C-7), 36.7 (C-22), 36.9 (C-10), 38.6 (C-1), 38.7 (C-4), 38.9 (C-20), 39.1 (C-19), 39.5 (C-8), 42.0 (C-14), 47.5 (C-9), 48.0 (C-17), 52.8 (C-18), 55.2 (C-5), 64.3 (—COOCH$_2$—), 79.0 (C-3), 125.5 (C-12), 138.2 (C-13), 177.6 (C-28). EIMS (70 eV) m/z (% rel. int.): 540 [M]$^+$ (5). HREIMS: calcd for C$_{36}$H$_{60}$O$_3$: 540.4542. found: 540.4538.

3'-Methyl-2'-butenyl 3β-hydroxyurs-12-en-28-oate (compound 9): Compound 9 is prepared from 1 (50 mg, 0.11 mmol) following the general procedure described for esterification at C-17 carboxylic acid using 1-bromo-3-methyl-2-butene as alkyl halide moiety. Compound 9 was obtained as a white solid (17.5 mg, 0.03 mmol, 30%), $[\alpha]_D^{25}$=+36. IR (KBr): 3447, 1720 cm$^{-1}$. $^1$H NMR (CDCl$_3$): δ 0.75 (3H, s, H-25), 0.77 (3H, s, H-24), 0.85 (3H, d, J=6.4 Hz, H-30), 0.92 (3H, s, H-26), 0.94 (3H, d, J=6.4 Hz, H-29), 0.99 (3H, s, H-27), 1.07 (3H, s, H-23), 1.68 (3H, s, —CH=C(CH$_3$)$_2$), 1.74 (3H, s, —CH=C(CH$_3$)$_2$), 2.23 (1H, d, J=11.2 Hz, H-18), 3.23 (1H, dd, J=10.8, 4.8 Hz, H-3α), 4.48 (1H, dd, J=10.4, 7.2 Hz, —COOCHH—), 4.51 (1H, dd, J=10.4, 7.6 Hz, —COOCHH—), 5.24 (1H, t, J=4.0 Hz, H-12), 5.30 (1H, t, J=7.6 Hz, —CH=C(CH$_3$)$_2$). $^{13}$C NMR (CDCl$_3$): δ 15.4 (C-24), 15.6 (C-25), 17.0 (C-11), 17.1 (C-26), 18.0 (—CH=C(CH$_3$)$_2$), 18.3 (C-6), 21.2 (C-29), 23.3 (C-27), 23.5 (C-30), 24.2 (C-16), 25.8 (—CH=C(CH$_3$)$_2$), 27.2 (C-2), 28.0 (C-15), 28.1 (C-23), 30.7 (C-21), 33.1 (C-7), 36.6 (C-22), 37.0 (C-10), 38.6 (C-1), 38.7 (C-4), 38.8 (C-20), 39.1 (C-19), 39.5 (C-8), 42.1 (C-14), 47.6 (C-9), 48.0 (C-17), 52.9 (C-18), 55.2 (C-5), 61.0 (—COOCH$_2$—), 79.0 (C-3), 119.1 (—CH=C(CH$_3$)$_2$), 125.5 (C-12), 138.1 (—CH=C(CH$_3$)$_2$), 138.2 (C-13), 177.5 (C-28). ESIMS (70 eV) m/z (% rel. int.): 547. HRESIMS: calcd for C$_{35}$H$_{56}$O$_3$Na: 547.4127. found: 547.4123.

2'-Hydroxyethyl 3β-hydroxyurs-12-en-28-oate (compound 10): Compound 10 is prepared from compound 1 (50 mg, 0.11 mmol) following the general procedure described for esterification at C-17 carboxylic acid using 2-chloroethanol as alkyl halide moiety. Compound 10 is obtained as a white solid (28.5 mg, 0.06 mmol, 52%), $[\alpha]_D^{25}$=+35. IR (KBr): 3433, 1718 cm$^{-1}$. $^1$H NMR (CDCl$_3$): δ 0.76 (3H, s, H-25), 0.77 (3H, s, H-24), 0.86 (3H, d, J=6.4 Hz, H-30), 0.91 (3H, s, H-26), 0.94 (3H, d, J=6.4 Hz, H-29), 1.01 (3H, s, H-27), 1.09 (3H, s, H-23), 2.24 (1H, d, J=10.8 Hz, H-18), 3.21 (1H, dd, J=11.2, 4.8 Hz, H-3α), 3.79 (2H, m, —COOCH$_2$—), 4.08 (1H, ddd, J=11.6, 5.6, 3.2 Hz, —CHHOH), 4.20 (1H, ddd, J=11.6, 6.0, 3.6 Hz, —CHHOH), 5.26 (1H, t, J=3.6 Hz, H-12). $^{13}$C NMR (CDCl$_3$): δ 15.4 (C-24), 15.6 (C-25), 17.0 (C-11), 17.1 (C-26), 18.3 (C-6), 21.1 (C-29), 23.3 (C-27), 23.5 (C-30), 24.2 (C-16), 27.2 (C-2), 27.9 (C-15), 28.1 (C-23), 30.6 (C-21), 33.0 (C-7), 36.7 (C-22), 36.9 (C-10), 38.6 (C-1), 38.7 (C-4), 38.8 (C-20), 39.1 (C-19), 39.5 (C-8), 42.2 (C-14), 47.5 (C-9), 48.3 (C-17), 53.0 (C-18), 55.2 (C-5), 61.4 (—CH$_2$OH), 66.0 (—COOCH$_2$—), 79.0 (C-3), 125.3 (C-12), 138.9 (C-13), 177.9 (C-28). EIMS (70 eV) m/z (% rel. int.): 500 [M]$^+$ (3). HREIMS: calcd for C$_{32}$H$_{52}$O$_4$: 500.3865. found: 500.3863.

Tert-Butoxycarbonylmethyl 3β-hydroxyurs-12-en-28-oate (compound 11): Compound 11 is prepared from compound 1 (50 mg, 0.11 mmol) following the general procedure described for esterification at C-17 carboxylic acid using chloroacetic acid tert-butyl ester as alkyl halide moiety. Compound 11 is obtained as a white solid (38.9 mg, 0.07 mmol, 62%), $[\alpha]_D^{25}$=+20. IR (KBr): 3447, 1733 cm$^{-1}$. $^1$H NMR (CDCl$_3$): δ 0.72 (3H, s, H-25), 0.78 (3H, s, H-24), 0.86 (3H, d, J=6.4 Hz, H-30), 0.91 (3H, s, H-26), 0.94 (3H, d, J=6.4 Hz, H-29), 0.98 (3H, s, H-27), 1.08 (3H, s, H-23), 1.45 (9H, s, —C(CH$_3$)$_3$), 2.25 (1H, d, J=11.2 Hz, H-18), 3.21 (1H, dd, J=9.6, 3.6 Hz, H-3α), 4.42 (2H, m, —COOCH$_2$—), 5.25 (1H, t, J=3.6 Hz, H-12). $^{13}$C NMR (CDCl$_3$): δ 15.4 (C-24), 15.6 (C-25), 16.9 (C-26), 17.0 (C-11), 18.3 (C-6), 21.2 (C-29), 23.3 (C-27), 23.5 (C-30), 24.2 (C-16), 27.2 (C-2), 28.0 (—OC(CH$_3$)$_3$), 28.0 (—OC(CH$_3$)$_3$), 28.1 (C-23), 29.7 (—OC(CH$_3$)$_3$), 30.6 (C-21), 33.0 (C-7), 36.5 (C-22), 36.9 (C-10), 38.6 (C-1), 38.7 (C-4), 38.8 (C-20), 39.1 (C-19), 39.5 (C-8), 42.0 (C-14), 47.6 (C-9), 48.0 (C-17), 52.7 (C-18), 55.2 (C-5), 60.9 (—COOCH$_2$—), 79.0 (C-3), 125.7 (C-12), 138.0 (C-13), 167.1 (—CH$_2$CO—), 176.7 (C-28). EIMS (70 eV) m/z (% rel. int.): 570 [M]$^+$ (6). HREIMS: calcd for C$_{36}$H$_{58}$O$_5$: 570.4283. found: 570.4291.

EXAMPLE 2

This example illustrates the preparation of compounds 12-17.

Figure 2:
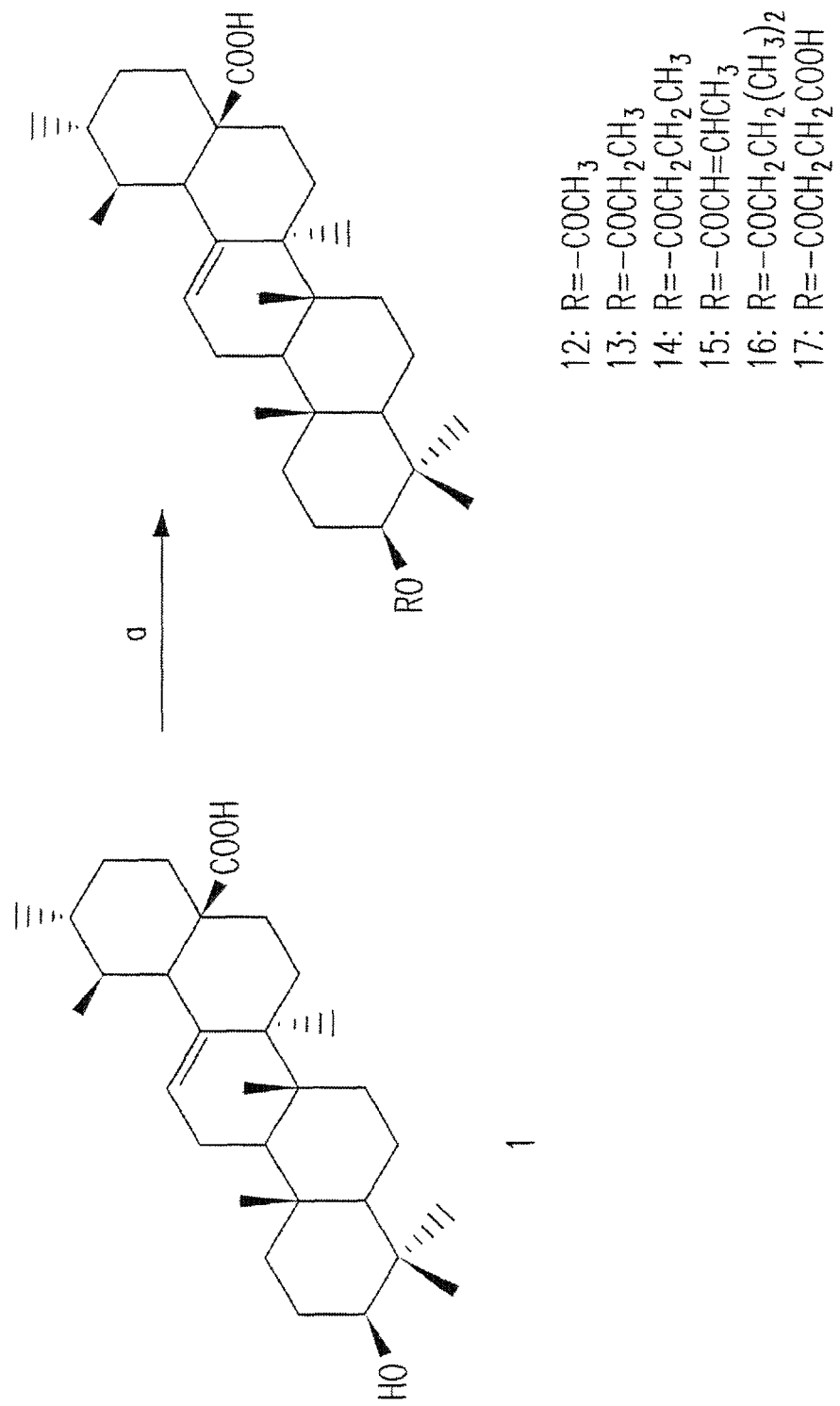
FIG. 2 is a flow chart illustrating the processes in the present invention for synthesizing the compounds 12-17, wherein each number represents a different compound.

Please refer to FIG. 2, which is a flow chart illustrating the processes in the present invention for synthesizing the compounds 12-17, wherein each number represents a different compound.

The hydroxyl group at C-3 in the ring A of the compound 1 is treated with various anhydrides, such as anhydrous acetic acid and various carboxylic acids, to form different esters (compounds 12-17). The reaction additives may be DCC, DMAP, pyridine and so on.

For example, compound 1 (50 mg, 0.11 mmol) is dissolved in different anhydride (1 mL) and pyridine (1 mL), and the solution is stirred at room temperature for 6 h. The reaction mixture is added water (10 mL) and partitioned with DCM (15 mL×3). The organic solution is dried over Na$_2$SO$_4$ and concentrated in vacuo to give crude product. The crude product is purified by chromatography on a column of silica gel eluted with EtOAc/n-hexane to obtain compounds 12-17.

EXAMPLE 3

This example illustrates the preparation of compounds 18-24.

Figure 3:
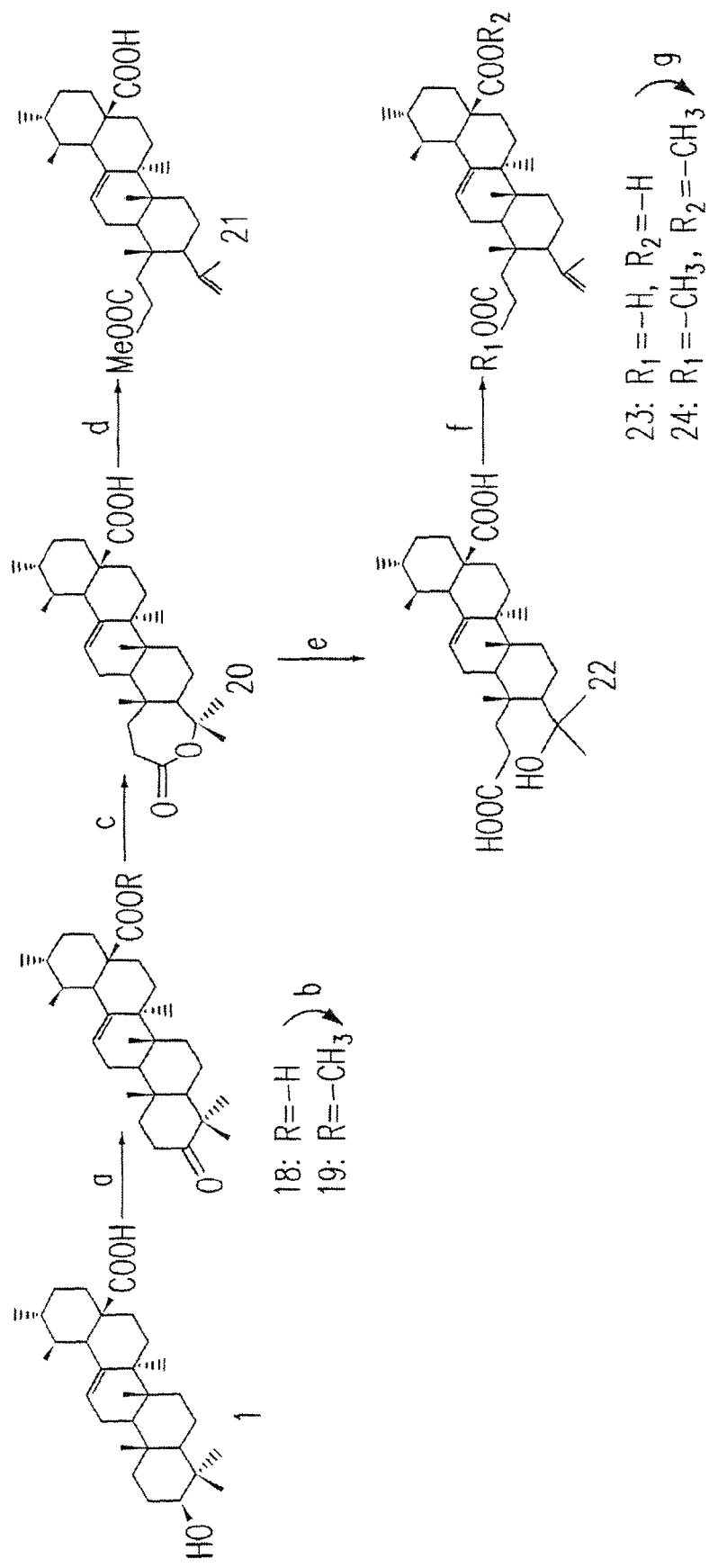
FIG. 3 is a flow chart illustrating the processes in the present invention for synthesizing the compounds 18-24, wherein each number represents a different compound.

Please refer to FIG. 3, which is a flow chart illustrating the processes in the present invention for synthesizing the compounds 18-24, wherein each number represents a different compound.

Compound 1 is oxidized to the 3-keto compound 18 with CrO$_3$ in DMF (step a). The treatment of 3-oxo-derivative 18 with m-chloroperbenzoic acid (m-CPBA) afford lactone compound 20 (step c). Compound 18 in anhydrous MeOH/benzene is esterified with trimethylsilyldiazomethane (TMSCHN$_2$) at room temperature to yield compound 19 (step b). Lactone 20 is cleavaged in the appropriate amount of MeOH and H$_2$SO$_4$ as the catalyst to yield seco-compound 21 (step d), and is cleavaged with KOH in MeOH to yield seco-compound 22 (step e). Seco-Compound 22 in MeOH reacts with $H_2SO_4$ to yield seco-compound 23 (step f). Compound 23 in anhydrous MeOH/benzene is esterified with trimethylsilyldiazomethane ($TMSCHN_2$) at room temperature to yield compound 24 (step g).

The detailed embodiments for the preparation of the compounds 20-22 are described as follows.

4-Hydroxy-3,4-seco-ursan-12-en-28-oic acid 3,4 lactone (compound 20): A mixture of compound 18 (150 mg, 0.3 mmol) and 70-75% 3-chloroperoxybenzoic acid (200 mg, 0.8-0.9 mmol) in $CHCl_3$ (10 mL) is stirred at room temperature for 72 h. More chloroform (20 mL) is added and the organic layer is washed with aq KI (5%), aq $Na_2SO_3$, water, aq $NaHCO_3$ solutions. The solution is extracted with $CHCl_3$ (30 mL×3), dried over $Na_2SO_4$, and concentrated in vacuo to give the crude product. The crude product is purified by chromatography on a column of silica gel eluted with EtOAc/DCM (1:6) to obtain compound 20 (91 mg, 0.19 mmol, 59%) as a white powder, $[\alpha]_D^{25}=+49$. IR (KBr): 3448, 1756, 1714 $cm^{-1}$. $^1H$ NMR ($CDCl_3$): δ 0.80 (3H, s, H-25), 0.85 (3H, d, J=6.4 Hz, H-30), 0.95 (3H, d, J=6.0 Hz, H-29), 1.01 (3H, s, H-26), 1.07 (3H, s, H-27), 1.26 (3H, s, H-24), 1.28 (3H, s, H-23), 2.20 (1H, d, J=11.2 Hz, H-18), 5.25 (1H, t, J=3.6 Hz, H-12). $^{13}C$ NMR ($CDCl_3$): δ 13.6 (C-25), 16.8 (C-26), 17.0 (C-11), 19.7 (C-24), 20.8 (C-27), 21.1 (C-30), 23.3 (C-29), 23.9 (C-6), 24.0 (C-16), 27.9 (C-15), 29.6 (C-7), 30.5 (C-21), 31.8 (C-2), 36.6 (C-22), 37.0 (C-9), 38.8 (C-20), 39.0 (C-19), 42.1 (C-14), 45.3 (C-8), 47.9 (C-17), 52.5 (C-5), 55.2 (C-18), 74.9 (C-4), 125.3 (C-12), 138.1 (C-13), 175.8 (C-3), 182.8 (C-28). EIMS (70 eV) m/z (% rel. int.): 470 [M]$^+$ (2.3). HREIMS: calcd for $C_{30}H_{46}O_4$: 470.3395. found: 470.2825.

Methyl 3,4-seco-ursan-4(23), 12-dien-28-oic 3-oat (compound 21): A mixture of compound 18 (100 mg, 0.2 mmol) and 70-75% 3-chloroperoxybenzoic acid (100 mg, 0.4-0.5 mmol) in $CHCl_3$ (10 mL) is stirred at room temperature for 72 h. The mixture is concentrated to dryness under reduced pressure, added MeOH (10 mL) and c-$H_2SO_4$ (three drops), and stirred at room temperature for 24 h. The mixture is concentrated to dryness under reduced pressure again, washed with aq $NaHCO_3$ solution, extracted with $CHCl_3$ (20 mL×3), dried over $Na_2SO_4$, and concentrated in vacuo to give the crude product. The crude product is purified by chromatography on a column of silica gel eluted with EtOAc/n-hexane (1:3) to obtain compound 21 (22.0 mg, 0.05 mmol, 21%) as a white powder, $[\alpha]_D^{25}=+8$. IR (KBr): 3461, 1735, 1693 $cm^{-1}$. $^1H$ NMR ($CDCl_3$): δ 0.82 (3H, s, H-27), 0.86 (3H, d, J=6.4 Hz, H-30), 0.92 (3H, s, H-25), 0.94 (3H, d, J=6.4 Hz, H-29), 1.09 (3H, s, H-26), 1.72 (3H, s, H-24), 2.25 (1H, d, J=11.2 Hz, H-18), 3.65 (3H, s, —$COOCH_3$), 4.64 (1H, s, —C=CHH), 4.86 (1H, s, —C=CHH), 5.26 (1H, t, J=3.2 Hz, H-12). $^{13}C$ NMR ($CDCl_3$): δ 17.0 (C-11), 17.2 (C-26), 19.5 (C-25), 21.1 (C-29), 23.4 (C-27), 23.4 (C-24), 23.5 (C-30), 24.0 (C-16), 24.3 (C-6), 28.0 (C-15), 28.5 (C-2), 30.6 (C-21), 31.6 (C-1), 33.9 (C-7), 36.7 (C-22), 37.7 (C-9), 38.8 (C-20), 39.1 (C-19), 39.2 (C-8), 39.2 (C-10), 42.4 (C-14), 48.0 (C-17), 50.3 (C-5), 51.6 (—$COOCH_3$), 52.6 (C-18), 113.6 (C-23), 125.6 (C-12), 137.9 (C-13), 147.3 (C-4), 174.6 (C-28), 183.4 (C-3). EIMS (70 eV) m/z (% rel. int.): 484 [M]$^+$ (23). HREIMS: calcd for $C_{31}H_{48}O_4$: 484.3552. found: 484.3549.

3,4-seco-Ursan-4-hydroxy-12-en-3,28-dioic acid (compound 22): Compound 20 (30 mg, 0.06 mmol) in 5% methanolic KOH is kept at room temperature for 48 h. The organic layer is removed under pressure. The mixture is added water (10 mL) and extracted with EtOAc (10 mL×3) to give the crude product. The crude product is purified by column chromatography eluted with acetone:DCM (1:3) and MeOH to obtain compound 22 (15 mg, 0.03 mmol, 48%) as a white powder, $[\alpha]_D^{25}=+35$. IR (KBr): 3447, 1690 $cm^{-1}$. $^1H$ NMR ($CD_3OD$): δ 0.89 (3H, d, J=6.4, H-30), 0.91 (3H, d, J=6.4 Hz, H-29), 0.97 (3H, s, H-25), 1.10 (3H, s, H-26), 1.14 (3H, s, H-27), 1.25 (3H, s, H-24), 1.27 (3H, s, H-23), 2.22 (1H, d, J=11.6, H-18), 2.30 (1H, m, Hα-2), 2.49 (1H, m, Hβ-2), 5.27 (1H, t, J=3.6 Hz, H-12). $^{13}C$ NMR ($CD_3OD$): δ 17.7 (C-26), 17.8 (C-11), 18.1 (C-25), 20.6 (C-29), 21.6 (C-6), 23.4 (C-27), 23.8 (C-30), 24.1 (C-16), 28.3 (C-24), 29.2 (C-15), 30.4 (C-2), 31.8 (C-21), 32.7 (C-7), 33.7 (C-23), 35.7 (C-22), 38.1 (C-20), 40.1 (C-19), 40.6 (C-10), 42.1 (C-14), 43.8 (C-8), 49.0 (C-17), 52.9 (C-18), 53.0 (C-5), 54.4 (C-9), 76.2 (C-4), 127.2 (C-12), 139.4 (C-13), 181.7 (C-28 and C-3). ESIMS (70 eV) m/z: 511 [M+Na]$^+$. HRESIMS: calcd for $C_{30}H_{48}O_5Na$: 511.3399. found: 511.3402.

EXAMPLE 4

This example illustrates the cytotoxicities of compounds 1-24 against NTUB1 cells (human bladder cancer cell line), and cisplatin is used as the positive control.

In the present embodiment, cell culture and MTT assay is used for cell viability/proliferation. NTUB1, a human bladder cancer cell line, is established from a high-grade bladder cancer. NTUB1 cells are maintained in RPMI 1640 medium supplemented with 10% fetal bovine serum (FBS), 100 unit/mL penicillin-G, 100 μg/mL streptomycin, and 2 mM L-glutamine. The cells are cultured at 37° C. in a humidified atmosphere containing 5% $CO_2$.

For evaluating the cytotoxic effect of the tested compound with cisplatin, a modified 3-[4,5-dimethylthiazol-2-yl]-2,5-diphenyltetrazolium bromide (MTT, Sigma Chemical Co.) assay is performed. Briefly, the cells are plated at a density of 1800 cells/well in 96-well plates and incubated at 37° C. overnight before drug exposure. Cells are then cultured in the presence of graded concentrations of the test compound with or without various concentrations of cisplatin (Pharmacia & Upjohn, Milan, Italy) at 37° C. for 72 h. At the end of the culture period, 50 μL of MTT (2 mg/mL in PBS) is added to each well and allowed to react for 3 h. Following centrifugation of plates at 1000 g for 10 min, media are removed and 150 μL DMSO are added to each well. The proportions of surviving cells are determined by absorbance spectrometry at 540 nm using MRX (DYNEXCO) microplate reader. The cell viability is expressed as a percentage to the viable cells of control culture condition. The $IC_{50}$s of each group are calculated by the medianeffect analysis and presented as mean±standard deviation (SD).

Please refer to Table 1, which indicates the cytotoxicities of compounds 1-24 against NTUB1 cells ($IC_{50}$ values in μM) according to the mentioned embodiment. In Table 1, data are presented as mean±SD (n=5). Compounds 1-24 or cisplatin dissolved in DMSO are diluted with culture medium containing 0.1% DMSO, respectively. The control cells are treated with culture medium containing 0.1% DMSO. Cisplatin is used as a positive control. When 50% inhibition could not reached at the highest concentration, then % of viability is given in parentheses.

TABLE 1

| Compound | $IC_{50}$ (μM) |
|---|---|
| cisplatin | 3.27 ± 0.10 |
| 1 | 29.44 ± 1.90 |
| 2 | 37.13 ± 0 |
| 3 | 13.45 ± 0 |
| 4 | 18.28 ± 0 |
| 5 | 7.97 ± 0.48 |
| 6 | 15.64 ± 1.31 |
| 7 | 27.79 ± 1.63 |
| 8 | 26.16 ± 2.51 |
| 9 | 10.93 ± 2.01 |

TABLE 1-continued

| Compound | IC$_{50}$ (µM) |
|---|---|
| 10 | 19.53 ± 0 |
| 11 | >30 µM (64.85%) |
| 12 | 14.27 ± 2.14 |
| 13 | >30 µM (72.53%) |
| 14 | >30 µM (76.47%) |
| 15 | 11.94 ± 0 |
| 16 | 30.98 ± 4.14 |
| 17 | 8.65 ± 2.89 |
| 18 | 21.44 ± 15.50 |
| 19 | 29.57 ± 4.65 |
| 20 | >30 µM (63.91%) |
| 21 | >30 µM (62.77%) |
| 22 | >30 µM (56.04%) |
| 23 | 25.49 ± 1.46 |
| 24 | 15.63 1.82 |

As shown in Table 1, compound 1 and its derivatives show significant cytotoxic activities against NTUB1 cells. The esterification of C-17-COOH of 1 and 18 with methyl halide, such as compounds 2 and 19, decreases the cytotoxic activity against NTUB1 cells, but the esterification of compound 21, such as compound 24, enhances the cytotoxicity against NTUB1 cells.

The C-17-COOH of 1 esterified with the increased alkyl chain of halides such as compounds 3-8 and 10, or prenyl halide such as compound 9, indicates that all these compounds reveal stronger cytotoxicities than that of compound 2 against NTUB1 cells. The hydroxylation of C-17 ethyl ester of compound 3 such as compound 10 attenuate the cytotoxicity against NTUB1 cells.

The acetylation of C-3-OH of 1 enhances the cytotoxic activity while the C-3-OH of 1 modified to succinic ester, such as compound 17, potently enhances the cytotoxicity activity against NTUB1 cells.

Increasing carbon chain of ester moieties attenuates the cytotoxic effect while increasing the unsaturation of the same carbon chain of ester, such as compound 15, enhances cytotoxic effect.

The oxidation of C-3-OH (compounds 1 and 2) to keto group (compounds 18 and 19) increases cytotoxicities, while lactone derivative 20 obtained from compounds 18, and 3,4-seco-compounds 21 and 22 obtained from compound 20 weakens cytotoxic activities. Furthermore, the 3,4-seco-compound obtained from compound 22, such as compound 23, indicates the potently cytotoxic activity, and its dimethyl ester such as compound 24 further enhances the inhibitory effect on the cell growth.

According to the mentioned embodiment, it is clearly indicated that the 3,4-seco-compound with dimethyl ester moieties substituted as C-3 and C-17 obtained from cleavage of ring A displays stronger and concentration-dependent effects against NTUB1 cell growth.

EXAMPLE 5

This example illustrates the cytotoxic effect of compounds 5, 17 and 23 against cancer cells.

For further evaluating the cytotoxic effect of the ursolic acid derivatives and mechanisms of induced cancer cell death in vitro, cytotoxicities of selective compounds 5, 17 and 23 against PC3 and A549 are studied and compared with those of cytotoxicities against NTUB1 cells.

Figure 4A:
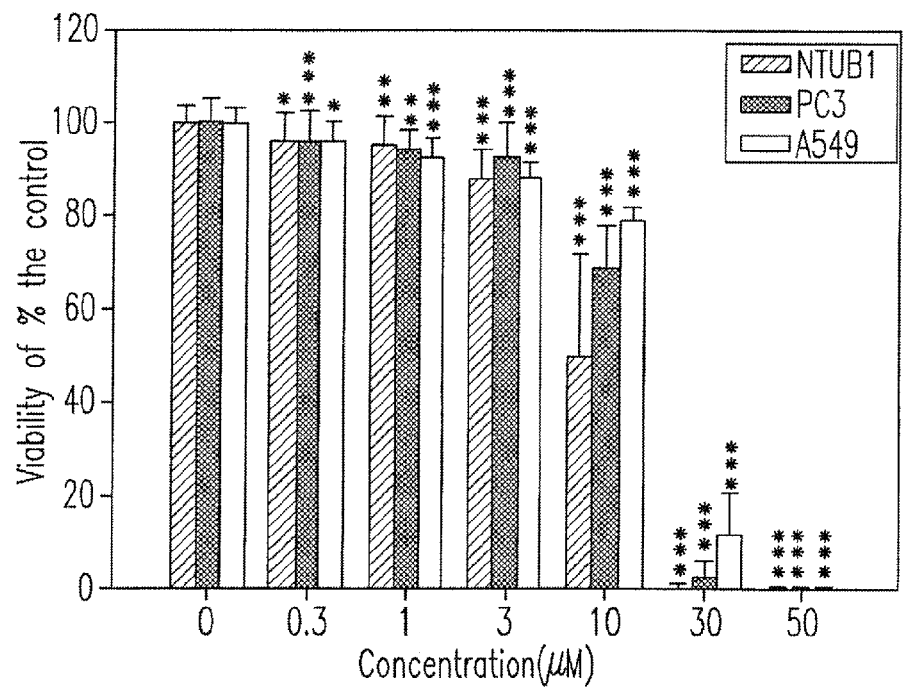
FIG. 4(A) is a diagram showing the cytotoxicities of the compound 5 against NTUB1, PC3 and A549 cells.
Figure 4B:
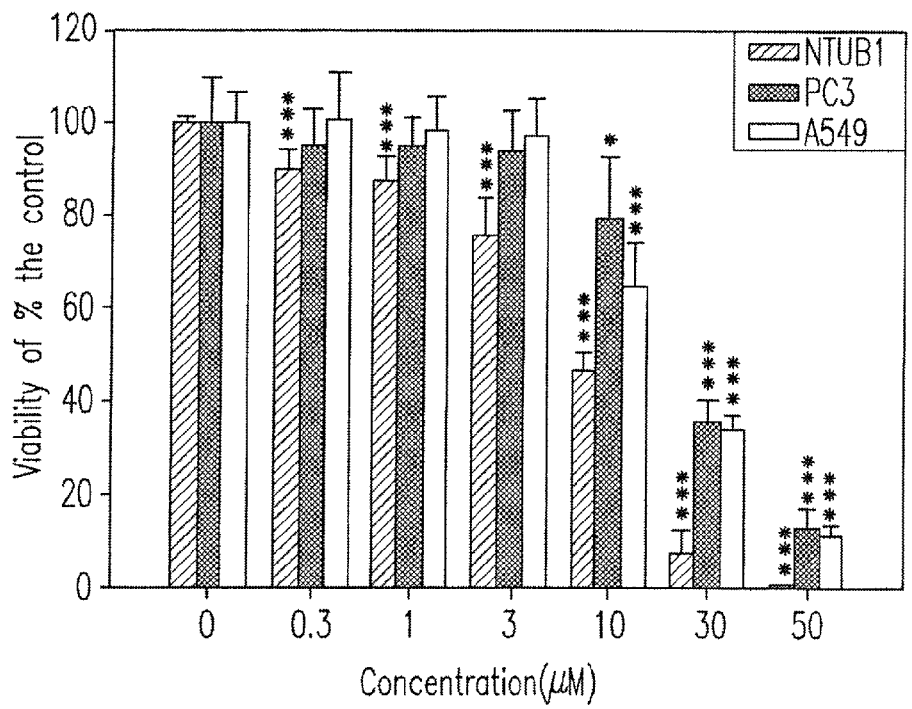
FIG. 4(B) is a diagram showing the cytotoxicities of the compound 17 against NTUB1, PC3 and A549 cells.
Figure 4C:
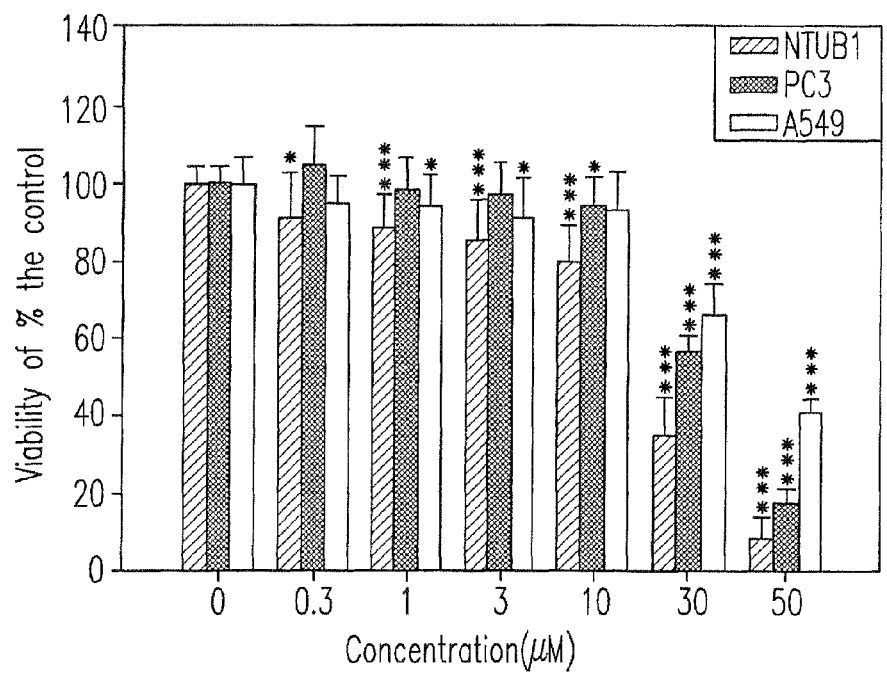
FIG. 4(C) is a diagram showing the cytotoxicities of the compound 23 against NTUB1, PC3 and A549 cells.

The cytotoxicities of compounds 5, 17 and 23 against NTUB1, PC3 and A549 cells are analyzed by the processes similar to those described in Example 4. Please refer to FIGS. 4(A) to 4(C), which indicate the analyzed results of the cytotoxicities of compounds 5, 17 and 23, respectively, wherein cell viability is assessed by the MTT assay after treating with different concentrations of compounds for 72 h. The data shown in FIGS. 4(A) to 4(C) represent mean±SD (n=3) for one experiment performed in triplicate. The symbols, "*" represents p<0.05, "" represents p<0.01, and "*" represents p<0.001, compared to the control value, respectively.

As shown in FIGS. 4(A) to 4(C), compounds 5, 17 and 23 do not exhibit stronger cytotoxic effects against PC3 and A549 cells than those of cytotoxicities against NTUB1 cells while 50 µM compounds 5, 17 and 23 indicate same cytotoxic effect against these three human cancer lines.

EXAMPLE 6

This example illustrates the anti-inflammatory activities of compounds 5, 7-11, 20 and 21. The anti-inflammatory activities of compounds 5, 7-11, 20 and 21 are studied in vitro for their inhibitory effects on chemical mediators released from neutrophils, mast cells or macrophages of rat.

Please refer to Table 2, which illustrates the inhibitory effects of compounds 5, 7-11, 20 and 21 on the accumulation of $NO_2^-$ (Experiment A), superoxide anion formation (n mol/106 cells/30 min) from rat neutrophils stimulated with PMA (Experiment B), and the release of β-glucuronidase from rat peritoneal mast cells stimulated with compound 48/80 (Experiment C). In Table 2, when 50% inhibition could not be reached at the highest concentration, the percentage of inhibition at 30 µM is given.

TABLE 2

| | IC$_{50}$$^a$(µM) | | |
|---|---|---|---|
| Compound | A<br>$NO_2^-$ | B<br>Superoxide anion<br>formation | C<br>β-glucuronidase |
| 5 | 45.3 ± 7.0% | | |
| 7 | 29.8 ± 3.3% | 10.8 ± 2.2 | |
| 8 | | 11.5 ± 0.9 | |
| 9 | 45.2 ± 5.9% | 6.1 ± 1.9 | |
| 10 | 33.1 ± 7.2% | | |
| 11 | 21.7 ± 6.5 | | |
| 20 | 41.0 ± 9.6% | | |
| 21 | 15.6 ± 2.5 | | 29.3 ± 2.1% |
| Positive control$^b$ | 5.0 ± 1.5 | 7.3 ± 0.6 | 12.4 ± 1.6 |

$^a$When 50% inhibition could not be reached at the highest concentration, the percentage of inhibition at 30 µM is given in Table.
$^b$N-(3-aminomethyl)benzylamide (1400 W), trifluoperazine, and mepacrine were used as positive control for A, B, or C, respectively.

In the Experiment A, Nitric oxide (NO) in the cell medium is determined by the Griess reaction, and N-(3-aminomethyl) benzylamide (1400 W) is used as a positive control.

In the Experiment B, superoxide anion generation is measured in terms of superoxide dismutase-inhibitable cytochrome c reduction. Neutrophils isolated from the peripheral blood of the rats are washed and suspended in Hanks' balanced salt solution (HBSS). Neutrophil suspension is preincubated with DMSO or drugs, and then superoxide dismutase (SOD) or HBSS is added into the blank and test wells, respectively. The final volume of DMSO in the reaction mixture is ≤0.5%. After addition of cytochrome c, reaction is initiated by challenge with PMA (3 nM). Thirty minutes later, the reaction is terminated by centrifugation and the absorbance changes of supernatant are monitored at 550 nm in a microplate reader. The superoxide anion generation is measured in terms of superoxide dismutase-inhibitable cytochrome c reduction. Trifluoperazine is used as a positive control for the Experiment B.

In the Experiment C, Heparinized Tyrode's solution is injected into the peritoneal cavity of exsanguinated rat (Sprague-Dawley, 250-300 g). After abdominal massage, cells in the peritoneal fluid are harvested and then separated in 38% bovine serum albumin (BSA) in glucose-free Tyrode's solution. Cell pellets are washed and suspended in Tyrode's solution with 0.1% BSA to 1×106 cell/mL. Cell suspension is then preincubated at 37° C. with DMSO or drugs for 5 min. The final volume of DMSO in the reaction mixture is ≤0.5%. Fifteen min after the addition of compound 48/80 (10 mg/mL), β-glucuronidase (phenolphthalein-β-glucuronide as substrate, 550 nm) in the supernatant is determined. The total content of β-glucuronidase is measured after treatment of the cell suspension with Triton X-100, and the percentage release is calculated. Mepacrine is used as the positive control for the Experiment C.

EXAMPLE 7

This example illustrates the effect of compounds 5, 17 and 23 on intracellular ROS levels and cell cycle in NTUB1 cells.

As described in the background of the invention, ROS induce programmed cell death or necrosis, induce or suppress the expression of many genes, and activate cell signaling cascades. ROS cause a wide range of adaptive cellular responses ranging from transient growth arrest to permanent growth arrest, to apoptosis or to necrosis, dependent on the level of ROS. These responses allow organism to remove damage caused by ROS or allow organisms to remove damage cells.

Exposure of cells to 10 µM cisplatin, 40 µM compound 5, 20 µM compound 23, and 50 µM compound 23 for 24 h cause a significant increase in intracellular ROS while this effect is inhibited by N-acetyl-cysteine (NAC, a thiol antioxidant agent). Furthermore, exposure of cells to 10 µM cisplatin, 20 and 40 µM compound 5, and 20 and 50 µM compound 23 for 48 h also cause a significant increase in intracellular ROS while this effect does not be inhibited by NAC.

Whereas cell proliferation and differentiation are specifically in the G1 phase and the G1-S transition in the cell cycle, the oncogenic progress exerts its greatest effect by targeting particular regulators of G1 phase progression.

The effects of positive control cisplatin, compounds 5, 17 and 23 on cell cycle progression are determined by using fluorescence-activated cell sorting (FACS) analysis in propidium iodide-stained NTUB1 cells.

8×10^5 cells are plated and treated with various concentrations of cisplatin and various concentrations of compounds 5, 17 and 23 for 24 or 48 h, respectively. These cells are harvested by trypsinization, washed with 1×PBS, and fixed in ice-cold MeOH at −20° C. After overnight incubation, the cells are washed with PBS and incubated with 50 µg/mL propidium iodide (Sigma, Co) and 50 µg/mL RNase A (Sigma, Co) in PBS at room temperature for 30 min. The fractions of cells in each phase of cell cycle are analyzed using FACScan flow cytometer and CellQuest software (Becton Dickinson).

As to the quantitative analysis of intracellular ROS, the flow cytometry analysis is also adopted. Cells are plated and treated as above-mentioned conditions. Ten-micromolar dichlorofluorescein diacetate (DCFH-DA; Molecular Probes, Eugene, Oreg.) is added to the treated cells 30 min prior harvest. The cells are collected by trypsinization and washed with PBS. The green fluorescence of intracellular DCF (2',7'-dichlorofluorescein) is then analyzed immediately by FACScan flow cytometer with a 525-nm band pass filter (Becton Dickinson).

The analysis results of the mentioned examples are described as follows. Treatment with 10 and 20 µM cisplatin for 24 h leads to a dose dependent accumulation of cells in the G1 phase with a concomitant increase in the population of sub-G1 phase. Treatment with 20 and 40 µM compound 5, and 20 and 50 µM compound 23 for 24 h induces G1 phase arrest in a dose-dependent manner, accompanied by an increase in the apoptotic cell death, while treatment with 20-40 µM compound 17 for 24 h induces G2/M arrest before accumulation of cells in sub-G1 phase.

Moreover, treatment with 10 µM cisplatin for 48 h results in S phase arrest while treatment with 20-40 µM compound 5 and 20-50 µM compound 23 for 48 h arrests G2/M phase before accumulation of cells in sub-G1 phase.

It has been known that cellular ROS are essential to cell survival, but the effect of ROS on cell is complex. Experimentally, a low concentration of $H_2O_2$ causes a moderate increase in proliferation of many tumor cell lines, whereas a higher level results in slowed growth, cell cycle arrest, and apoptosis or even necrosis.

In the present example, treatment of cells with compound 5 for 24 and 48 h exhibits induced G1 phase and G2/M arrest, respectively, and increases the amount of ROS in cells.

Based on the mentioned experiments, it indicates that the cell cycle arrest and apoptosis induced by compound 5 are correlated with ROS. Treatment of cells with 20 and 40 µM compound 17 for 24 h induces G2/M arrest before accumulation of cells in sub-G1 phase. The induction of increased amount of ROS and G1 phase arrest by treatment of cells with 20 and 50 µM compound 23 for 24 h. It also indicates that the induction of G1 phase arrest by treatment of cells with compound 23 for 24 h is due to the increased amount of ROS induced by compound 23 in cells. Treatment of cells with 20 µM compound 23 for 48 h results in G2/M phase arrest.

EXAMPLE 8

This example illustrates the effect of the ursolic acid derivatives upon the inhibition of tubulin polymerization.

All inhibition of tubulin polymerization has been implicated in G2/M phase cell cycle arrest in various cancer cell lines. Accordingly, whether treatment of cells with 20 µM compound 23 for 48 h affects in vivo microtubular architecture is investigated in the present example. Microtubule assembly is analyzed by indirect immunofluorescence staining using an anti-tubulin antibody (Santa Cruz Biotechnology, Santa Cruz, Calif., USA).

NTUB1 cells plated on coverslips are treated with no compound as control, 10 nM taxol, 50 µM compound 23 for 24 h. After treatment, cells are fixed with 2% formaldehyde/PBS for 20 min, washed with PBS, and cold methanol (−20° C.) for 3 min. After washing with PBS, cells are added anti-α-tubulin monoclonal antibody (Sigma, Co) in PBS and incubated for 3 h at room temperature. Then cells are washed with PBS and reincubated with Rodamine-conjugated secondary antibody (Sigma, Co) in dark room for 1 h at room temperature. After being washed with PBS, coverslips are mounted with 80% glycerol in PBS and examined with Axioskop 2 plus fluorescence microscope.

Figures 5A, 5B, 5C:
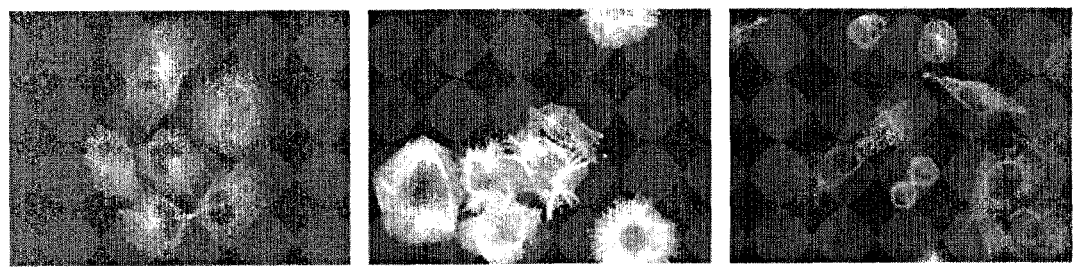
FIGS. 5(A) to 5(C) are diagrams showing the effects of taxol and compound 23 on microtubule assembly, wherein the cellular microtubules are observed by Axioskop 2 plus fluorescence microscope.

Please refer to FIGS. 5(A) to 5(C), which are diagrams showing the effects of taxol and compound 23 on microtubule assembly, wherein the cellular microtubules are observed by Axioskop 2 plus fluorescence microscope. FIG. 5(A) shows that untreated NTUB1 cells (control) show diffuse staining throughout the cytoplasm and dense perinuclear staining. FIG. 5(B) shows that treatment of cells with taxol results in a distinctive microtubule bundle that is likely due to stabilization of the rigid microtubule network. FIG. 5(C) shows that treatment with compound 23 results in that cells treated with compound 23 for 48 h prevents microtubule assembly in vivo by inhibiting tubulin polymerization. Accordingly, compound 23 reveals a partial mechanism by which compound 23 mediated through generation of ROS in NTUB1 cells induces inhibition of tubulin polymerization, G2/M cell cycle arrest, and apoptosis.

While the invention has been described in terms of what is presently considered to be the most practical and preferred embodiments, it is to be understood that the invention needs not be limited to the disclosed embodiments. On the contrary, it is intended to cover various modifications and similar arrangements included within the spirit and scope of the appended claims which are to be accorded with the broadest interpretation so as to encompass all such modifications and similar structures.

What is claimed is:

1. An ursolic acid derivative having a structure being one of

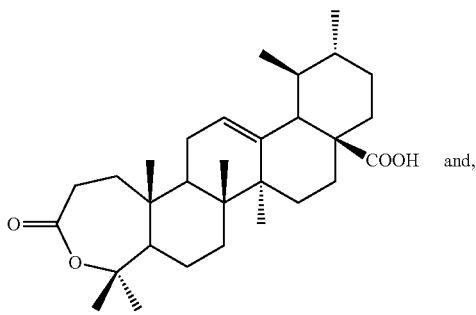

and,

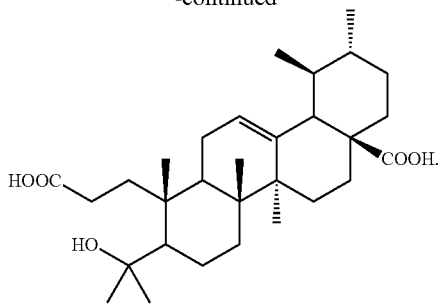

2. The ursolic acid derivative as claimed in claim 1, having at least one of an anticancer and an anti-inflammatory activities.

3. A pharmaceutical composition comprising the ursolic acid derivative as claimed in claim 1.

4. The pharmaceutical composition as claimed in claim 3, further comprising a pharmaceutically acceptable carrier.

5. The pharmaceutical composition as claimed in claim 3, having at least one of an anticancer and an anti-inflammatory effects.

6. The pharmaceutical composition as claimed in claim 3, further comprising a drug having an anticancer activity.

7. The pharmaceutical composition as claimed in claim 6, wherein the ursolic acid derivative enhances the anticancer activity of the drug.

* * * * *